(12) United States Patent
Lee

(10) Patent No.: US 9,492,232 B2
(45) Date of Patent: Nov. 15, 2016

(54) POWERED STEREOTACTIC POSITIONING GUIDE APPARATUS

(71) Applicant: Choon Kee Lee, Denver, CO (US)

(72) Inventor: Choon Kee Lee, Denver, CO (US)

( * ) Notice: Subject to any disclaimer, the term of this patent is extended or adjusted under 35 U.S.C. 154(b) by 349 days.

(21) Appl. No.: 14/187,285

(22) Filed: Feb. 23, 2014

(65) Prior Publication Data

US 2015/0238265 A1   Aug. 27, 2015

(51) Int. Cl.
| | | |
|---|---|---|
| A61B 19/00 | (2006.01) | |
| A61B 8/08 | (2006.01) | |
| A61B 10/02 | (2006.01) | |
| A61B 17/34 | (2006.01) | |
| A61B 8/00 | (2006.01) | |

(52) U.S. Cl.
CPC .......... *A61B 19/201* (2013.01); *A61B 8/0841* (2013.01); *A61B 34/20* (2016.02); *A61B 90/11* (2016.02); *A61B 8/463* (2013.01); *A61B 10/0233* (2013.01); *A61B 2017/3409* (2013.01); *A61B 2017/3413* (2013.01); *A61B 2034/2063* (2016.02)

(58) Field of Classification Search
CPC ....... A61B 10/0233–10/0283; A61B 17/3403; A61B 2017/3405–2017/3413; A61B 8/0833–8/085
USPC .............................................. 606/1, 129–130
See application file for complete search history.

(56) References Cited

U.S. PATENT DOCUMENTS

| | | |
|---|---|---|
| 5,623,931 A | 4/1997 | Wung |
| 5,941,889 A | 8/1999 | Cermak |
| 6,203,499 B1 | 3/2001 | Imling |
| 6,475,152 B1 | 11/2002 | Kelly, Jr. |
| 6,485,426 B2 | 11/2002 | Sandhu |
| 7,691,066 B2 | 4/2010 | Kosaku |
| 7,846,103 B2 | 12/2010 | Cannon, Jr. |
| 7,976,469 B2 | 7/2011 | Bonde |
| 8,057,487 B2 | 11/2011 | Chu |
| 8,073,529 B2 | 12/2011 | Cermak |
| 8,118,743 B2 | 2/2012 | Park |
| 8,216,149 B2 | 7/2012 | Oonuki |
| 8,241,301 B2 * | 8/2012 | Zhang ........................... 600/407 |
| 8,257,264 B2 | 9/2012 | Park |
| 8,496,593 B2 | 7/2013 | Park |
| 8,574,160 B2 | 11/2013 | Gorzitze |
| 2002/0058872 A1 | 5/2002 | Steininger |
| 2007/0073155 A1 | 3/2007 | Park |
| 2011/0313293 A1 | 12/2011 | Lindekugel |
| 2012/0059260 A1 | 3/2012 | Robinson |
| 2012/0184956 A1* | 7/2012 | Velusamy .......... A61B 17/3403 606/41 |

(Continued)

FOREIGN PATENT DOCUMENTS

| | | |
|---|---|---|
| DE | 19808220 A1 | 9/1999 |
| DE | 10015510 A1 | 4/2001 |
| SE | 524042 C2 | 6/2004 |

*Primary Examiner* — Victor Nguyen
*Assistant Examiner* — Jonathan Hollm

(57) ABSTRACT

The present invention presents an apparatus and methods to stereotactically guide insertion of invasive tubular devices to a tissue object of a living body. The apparatus comprises a powered positioning guide control assembly and a positioning guide assembly that is operably detachable from the powered positioning guide control assembly, and rotationally adjustable and lockable. The powered positioning guide control assembly encloses an ultrasound transducer to visualize and target the tissue object, and adjusts an insertion angle of an invasive tubular device placed in the positioning guide assembly.

11 Claims, 11 Drawing Sheets

(56) References Cited

U.S. PATENT DOCUMENTS

| | | | |
|---|---|---|---|
| 2012/0259220 A1* | 10/2012 | Sheldon | A61B 17/3403 600/439 |
| 2012/0259221 A1* | 10/2012 | Sheldon | A61B 8/462 600/439 |
| 2013/0066192 A1* | 3/2013 | Sarvestani | A61B 17/3403 600/424 |
| 2013/0197355 A1 | 8/2013 | Lee | |
| 2013/0225984 A1 | 8/2013 | Cheng | |
| 2014/0018671 A1* | 1/2014 | Li | A61B 6/5235 600/424 |

* cited by examiner

Figure 2
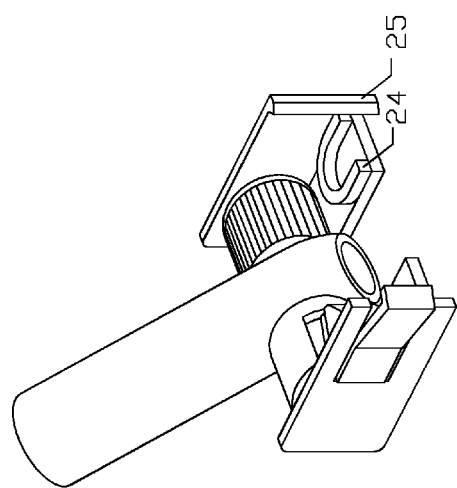
C
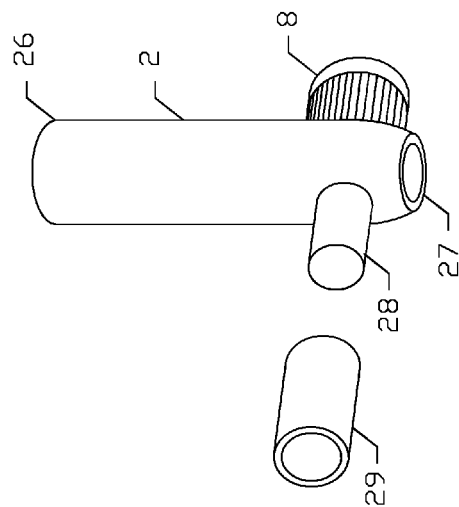
D
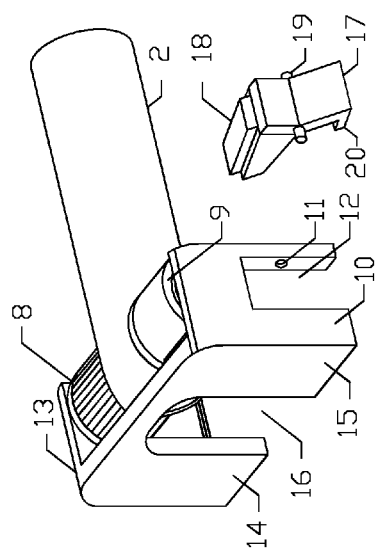
A
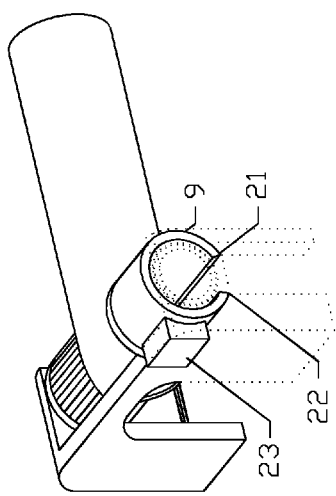
B

Figure 8
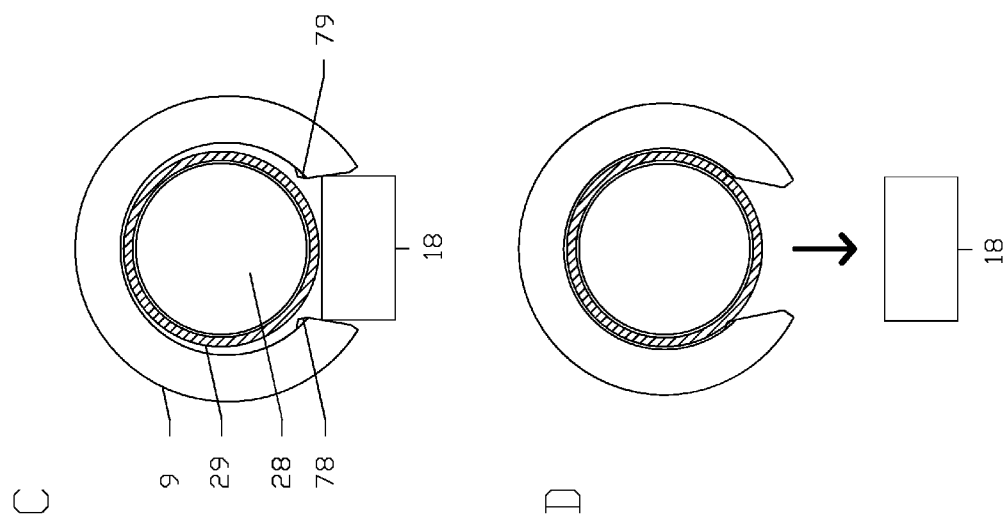
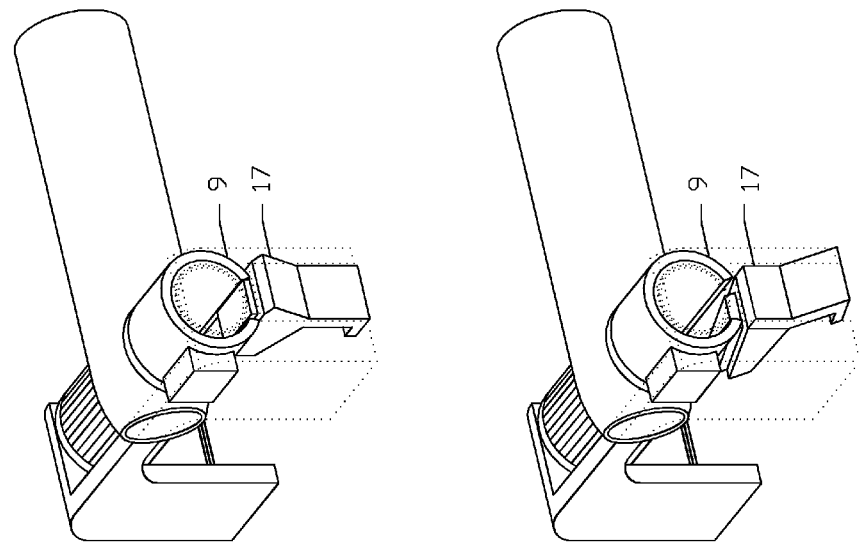

Figure 10
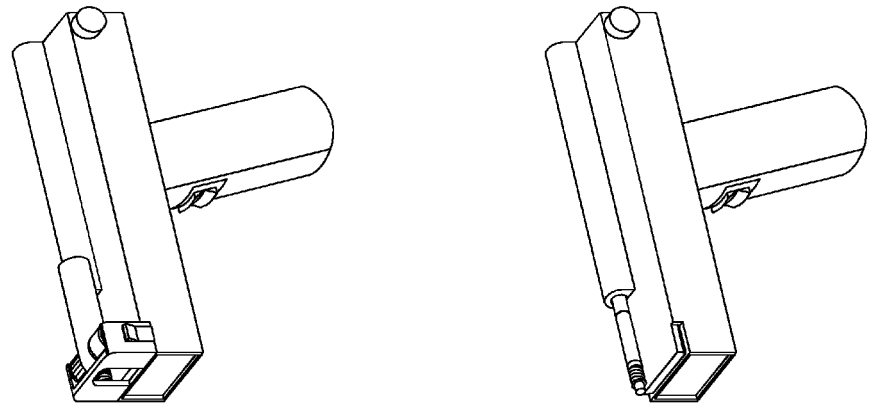
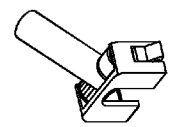
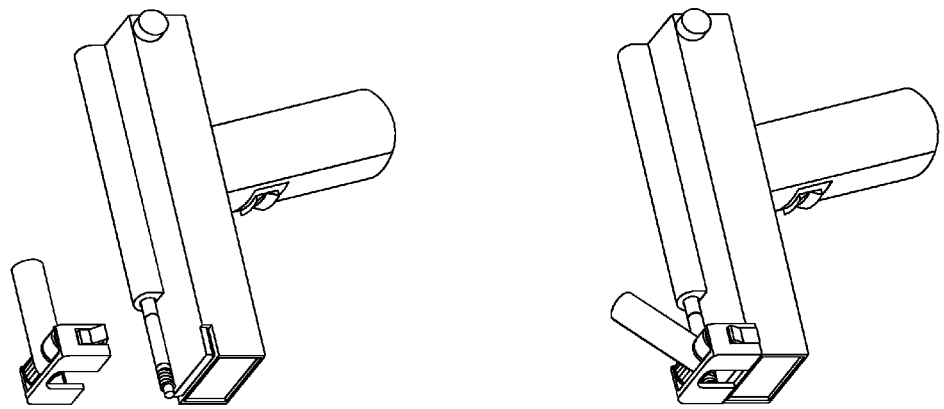
A
B
C
D

Figure 11
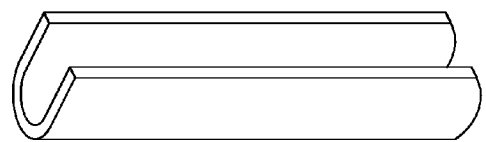
D
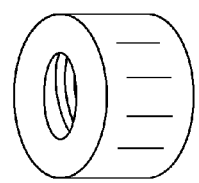
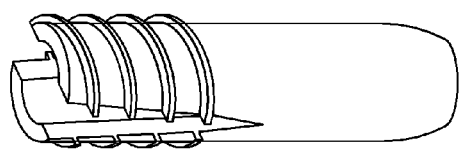
C
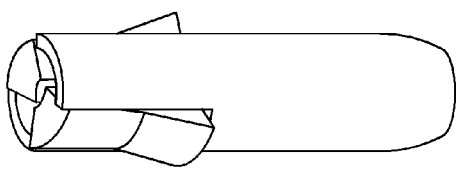
B-2
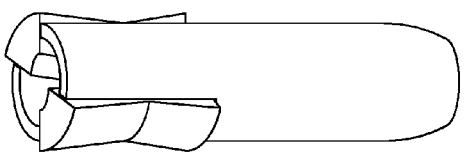
B-1
A

POWERED STEREOTACTIC POSITIONING GUIDE APPARATUS

CROSS REFERENCE TO RELATED APPLICATIONS

Attached please refer to the Information Disclosure Statement for the cross reference to related applications.

STATEMENT REGARDING FEDERALLY SPONSORED RESEARCH OR DEVELOPMENT

The present invention is not a federally sponsored research or development.

TECHNICAL FIELD

The present invention relates generally to the field of positioning guidance of insertion of invasive devices in a living body for medical purposes. More specifically, the present invention provides a powered apparatus and methods to guide introduction of tubular devices into a tissue using ultrasound.

BACKGROUND OF THE INVENTION

Visual guidance using ultrasound images has been successfully used for inserting core biopsy needles into tissue to procure tissue samples from a living body, resulting in high rates of sensitivity of tissue diagnosis. Accurate positioning of a biopsy needle by ultrasound guidance can be facilitated by providing a set of numerical positioning data for the biopsy needle such as an insertion length of the needle to reach an object from a skin and an insertion angle between a longitudinal axis of the needle and a horizontal axis of an ultrasound transducer visualizing the tissue object. Accuracy in positioning increases further by visualizing a linear alignment between a point of a contact portion of a transducer and a center of a tissue object and by reversibly adjusting an insertion angle based on position changes in the point of the contact portion of the transducer relative to the center of the tissue object.

Accuracy in positioning also depends on hand-eye coordination of an operator who handles and controls the visual guidance apparatus. Most commonly, the hand-eye coordination relies on a dominant hand and a three-dimensional view acquiesced by both eyes. Single-hand operation using a dominant hand tends to be more accurate in navigating structures than double-hand operation except for using the other non-dominant hand for stabilizing an object that is a target of the operation by the dominant hand. One way to increase the accuracy in positioning a biopsy needle by a visual guidance apparatus is to free the non-dominant hand for the most of a procedure except for holding steady either the apparatus or a target tissue region. It requires the dominant hand to take care of the most of the procedure, which could be achieved if the majority of operations of the apparatus are automated and controllable by one hand. In particular, the visual alignment and the adjustment of an insertion angle, which are two most important movements of the visual guidance apparatus, should be made controllable and reliably reproducible by one hand.

SUMMARY OF THE INVENTION

The present invention provides a powered apparatus that minimizes double-hand operations for guiding insertion of invasive tubular devices to tissue with ultrasonographically visualized targeting approaches to a tissue object. The invention provides a means to rotationally adjust insertion angle of invasive tubular devices to reach the tissue object, which can be monitored in an ultrasonographic field. The apparatus comprises a powered positioning guide control assembly and a positioning guide assembly that is releasably detachable from the positioning guide control assembly and operable. The positioning guide control assembly is configured to enclose an ultrasound transducer and coordinate adjusting an insertion angle of an invasive device by a powered motor assembly with arranging a linear alignment between a point of the transducer head and the tissue object in an ultrasonographic field.

In one embodiment, the positioning guide assembly is provided in one or a plurality of configurations, including a cross configuration which comprises an upright tubular positioning guide and a pair of transverse cylinders irreversibly attached at a right angle to each opposite side of a lower portion of an outer wall of the tubular positioning guide, respectively. One transverse cylinder is configured as a worm gear and serves for rotation of the tubular positioning guide and the other transverse cylinder provides the tubular positioning guide with rotational stability. The transverse cylinder for stability is slidably and rotatably housed in a cylinder overtube that is attached to a base panel located below said transverse cylinder.

In one embodiment, a cylinder overtube for a stabilizer cylinder of the tubular positioning guide has a horizontal slot for a length to accommodate a part of a lock and release lever which snaps in and out of said horizontal slot. An inner wall of the stabilizer cylinder overtube has a plurality of substantially linear threads. In between of an outer circumferential wall of the stabilizer cylinder and the inner wall of the stabilizer cylinder overtube, a thin nonslip tubular elastomer is provided, encasing the outer wall of said stabilizer cylinder. The horizontal slot of the stabilizer cylinder overtube is reversibly and circumferentially expandable to a degree upon engagement with the lock and release lever, which widens an inner tubular space of said stabilizer cylinder overtube. Widening of the inner tubular space allows friction-less rotation of both the elastomer and stabilizer cylinder inside said stabilizer cylinder overtube. Disengagement of the lock and release lever shrinks a circumference and the inner tubular space of said stabilizer cylinder overtube, which then holds fast both the tubular elastomer and stabilizer cylinder together. The stabilizer cylinder is fastened by friction generated by the circumferentially squeezed tubular elastomer encasing said stabilizer cylinder.

In one embodiment, the transverse cylinder of the tubular positioning guide configured as a worm gear meshes with a worm at a right angle to form a worm drive. The worm is configured to be longitudinally connected to an output shaft of a gearbox arrangement that is controllably driven by an electric motor. A proximal end of the worm is reversibly secured for axial rotation in a flange constructed on an upper surface of a base panel of the tubular positioning guide below the worm gear. A mid portion of the base panel is configured to provide an open space through which an invasive device passes from the tubular positioning guide to a tissue object. An opposite side of the base panel to a cylinder overtube attachment side is configured to provide reversible adhesion to a skin overlying a tissue object.

In one embodiment, the positioning guide assembly is configured to reversibly be fastened to the positioning guide control assembly by a snap-fit insertion of the lock and release lever to a notch provided on a proximal upper panel of the positioning guide control assembly. Insertion of said lock and release lever into said notch is coincided with engagement of said lever with the horizontal slot of the stabilizer cylinder overtube, which results in widening of the inner tubular space of said stabilizer cylinder overtube. Retracting said lock and release lever from said notch of the positioning guide control assembly disengages said lever from the horizontal slot of the stabilizer cylinder overtube, which releases the positioning guide assembly from the positioning guide control assembly and allows the stabilizer cylinder overtube to fasten the stabilizer cylinder of the tubular positioning guide, thereby preventing further rotation of the tubular positioning guide.

In one embodiment, the positioning guide control assembly is provided in one or a plurality of configurations including a modular configuration which comprises a transducer enclosure, a position alignment assembly, a powered positioning control assembly, a gear output shaft enclosure, a power and electronic control assembly and a handle assembly. The transducer enclosure is provided in a closed longitudinal box configuration with its proximal portion open to allow a face portion of a transducer to contact a distal part of the position alignment assembly via a solid gel panel. Proximal to the position alignment assembly, the transducer enclosure provides an open rectangular space to accommodate a second solid gel panel that contacts a skin overlying a tissue object. The transducer enclosure is configured to enclose the transducer in a manner to align longitudinal and horizontal axes of the transducer in parallel with longitudinal and horizontal axes of said transducer enclosure, respectively. Both the horizontal and longitudinal axes of the transducer are used as reference axes to calibrate angular displacement of the tubular positioning guide. A bottom portion of a distal portion of the transducer enclosure opens to the handle assembly through which electric cables pass. A distal end of the transducer enclosure adjoins a compartment for the powered positioning control assembly.

In one embodiment, the position alignment assembly is provided in one or a plurality of electromechanical configurations, which comprises a substantially ultrasound-transparent flat rectangular box and an electromagnetic pointing device. The flat rectangular box is configured as leakproof, is filled with an ultrasound-transparent liquid and located proximal to the face of the transducer. In one example, the position alignment assembly comprises a galvanometer-type electromagnetic pointing device that uses varying electric current or electric resistance to radially move a linear movable pointer around a center of said device. The linear movable pointer is configured to block ultrasound transmission, which is visualized in an ultrasonographic view.

In one embodiment, the positioning control assembly is provided in one or a plurality of configurations including a rectangular box configuration which encloses an electric motor, a gearbox and an angle encoder. The electric motor is irreversibly fixed to a distal wall of the positioning control assembly, with its rotor protruding longitudinally along the axis. A protruded portion of the rotor is configured as a longitudinal spur gear that meshes in parallel with a cylindrical spur gear. The cylindrical spur gear is connected to the angle encoder coaxially that measures rotational displacements of said cylindrical spur gear. The angle encoder is electronically connected to the power and electronic control assembly that relays an electronic information from said angle encoder of rotational displacements of the cylindrical spur gear to the electromagnetic pointing device of the position alignment assembly. The cylindrical spur gear meshes with another longitudinal spur gear that coaxially merges with the output shaft located outside the positioning control assembly. The output shaft is provided in one or a plurality of configurations and is housed in the gear output shaft enclosure. A proximal end of the output shaft protrudes from an opening located at a proximal end of the output shaft enclosure and is configured to be reversibly connected to a distal end of the worm. A switch located on an outer surface of the handle assembly is electrically connected to the positioning control assembly and is configured to turn on for a controllably variable duration and off the electric motor. Rotations of the electric motor are transmitted to the output shaft that in turn rotates the worm of the worm drive arrangement for the positioning guide assembly.

In one embodiment, the gear output shaft enclosure is provided in one or a plurality of configurations including a longitudinal tubular structure located on an upper surface of both the positioning control assembly and transducer enclosure. The output shaft enclosure has a proximal end having an opening through which the output shaft protrudes and a distal end which provides a central tubular cup to accommodate a distal end of the output shaft for axial rotation. The output shaft enclosure is configured to provide a means to reduce rotational friction between the output shaft and the output shaft enclosure, which includes a portion having a rolling-element bearing.

In one embodiment, the power and electronic control assembly is provided in one or a plurality of configurations including a rectangular box configuration which has an integrated circuit board, a segment digital display, a control knob connected to the integrated circuit board and a power source. The integrated circuit board is located distally and electronically connected to the segment digital display, the positioning control assembly, the position alignment assembly and the switch of the handle assembly. In one configuration, a compartment for replaceable batteries is located inside the positioning control assembly and connects batteries electrically with the integrated circuit board, the segment digital display, the positioning control assembly, the position alignment assembly and the switch of the handle assembly. The electronic control assembly is located distal to the positioning control assembly and the segment digital display is configured to be visible on a distal outer surface of the integrated circuit board. The segment digital display shows at least a digitized numerical information about a distance between a position of the linear movable pointer tangentially placed over the tissue object and said tissue object.

In another embodiment, the power and electronic control assembly is configured to control movements of the electromagnetic pointing device of the position alignment assembly upon an electronic input from the angle encoder. In this configuration, rotations of the worm gear of the positioning guide assembly by the electric motor of the positioning control assembly translate into ultrasonographically visualizable movements of the linear movable pointer of the electromagnetic pointing device of the position alignment assembly. In a two-dimensional ultrasonographic view, the linear movable pointer is configured to produce a thin vertically linear shadow line that can be distinguished readily from surrounding tissue images. Rotations of said worm gear are configured to match horizontal movements of said linear movable pointer in ways that a longitudinal axis of an invasive device at an insertion angle in the positioning guide assembly crosses a linear shadow line at a center of a tissue object in the two-dimensional ultrasonographic view.

In one embodiment, a distance (a) from a point of a proximal end of the transducer to a center of a tissue object is calculated by a substantially tangential placement of the proximal end of the transducer to a skin overlying the tissue object. A horizontal distance from a rotation center of the worm gear of the positioning guide assembly to a point of a linear movable pointer measures as (b). Using a simple trigonometry, a distance (h) of an invasive device from the rotation center of the worm gear to the center of the object equals a square root of $(a^2+b^2)$ and a sine of an angle ($\alpha$) of the worm gear is calculated as a ratio of (a) to (h). The horizontal distance (b) is variable based on a moving position of the linear movable pointer of the position alignment assembly.

In one embodiment, the control knob of the integrated circuit board is configured to provide the integrated circuit board with a numerical information of a measured distance (a) from the center of the tissue object vertically up to a point horizontal to the rotation center of the worm gear. The integrated circuit board calculates an angle ($\alpha$) based on the distance (a) and directs the positioning control assembly to rotate the worm gear of the positioning guide assembly to the angle ($\alpha$) in relation to the horizontal axis of the proximal end of the transducer head.

In one embodiment, the tubular positioning guide is provided in one or a plurality of configurations for a range of function of said tubular positioning guide. For conventional needle biopsy procedures, the tubular positioning guide is provided in a range of fixed tubular gauges to accommodate a range of needle sizes. For inserting vascular devices and their accessories, the tubular positioning guide is provided as semicircular tubular, which is to allow open access and insertion of more than one device during one session of a procedure and unobstructed interchangeable removal of devices. For therapeutic procedures such as insertion of a probe for radiofrequency ablation of a lesion, for an example, the tubular positioning guide is provided with devices to fasten such probes for an extended period of time.

BRIEF DESCRIPTION OF THE DRAWINGS

FIG. 2 shows a schematic example of individual components of the positioning guide assembly of the apparatus: FIG. 2A represents a positioning guide assembly and a lock and release lever shown separately for illustration; FIG. 2B shows a stabilizer cylinder overtube of the positioning guide assembly; FIG. 2C shows an internal view of the positioning guide assembly; FIG. 2D shows individual components of a tubular positioning guide.

FIG. 8 illustrates an schematic example of mechanisms of locking and unlocking of the tubular positioning guide; FIG. 8A shows an unlocked configuration of the tubular positioning guide; FIG. 8B shows a locked configuration; FIGS. 8C and 8D show a cross-sectional view of unlocked and locked configurations, respectively.

FIG. 10 illustrates a schematic example of a sequence of action of the present invention.

FIG. 11 shows schematic examples of various configurations of the tubular positioning guide.

DETAILED DESCRIPTION OF THE DRAWINGS

As described below, the present invention provides a powered positioning guide apparatus stereotactically targeting a tissue object and methods of use. It is to be understood that the descriptions are solely for the purpose of illustrating the present invention, and should not be understood in any way as restrictive or limited. Embodiments of the present invention are preferably depicted with reference to FIGS. 1 to 11, however, such reference is not intended to limit the present invention in any manner. The drawings do not represent actual dimension of devices, but illustrate the principles of the present invention.

Figure 1:
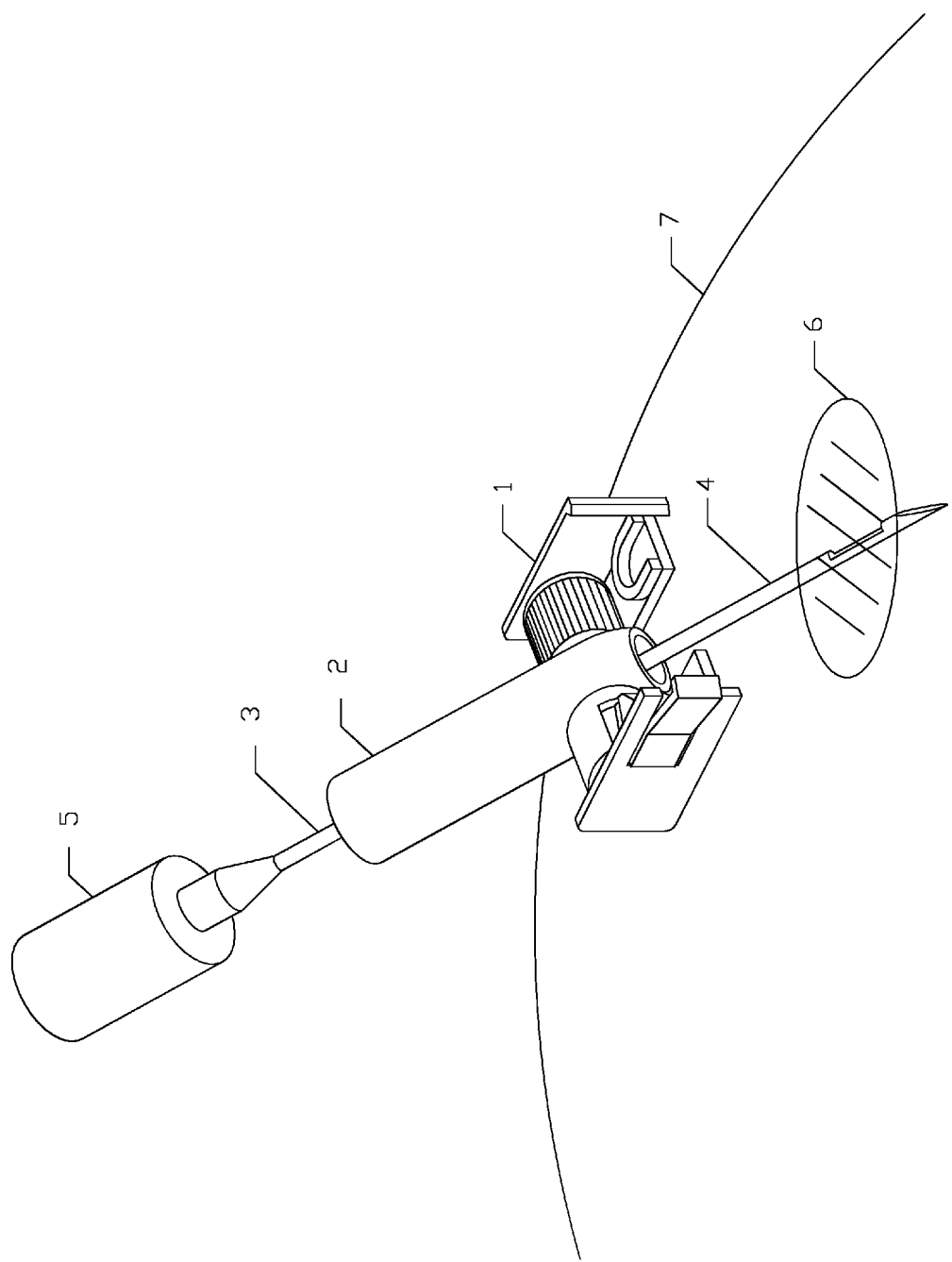
FIG. 1 shows a schematic illustration of an example of a positioning guide assembly of the present invention guiding a biopsy apparatus to a tissue object.

FIG. 1 shows a schematic example of a positioning guide assembly of the apparatus. FIG. 1-1 represents an angled and locked positioning guide assembly adherently attached to a skin 7 overlying a tissue object 6. In this particular example, the positioning guide assembly comprises a tubular positioning guide 2 through which a biopsy needle 3 of a biopsy apparatus 5 passes. A proximal portion 4 of the biopsy needle 3 is guided inside the tubular positioning guide 2 toward the tissue object 6.

FIG. 2 shows a schematic example of individual components of the positioning guide assembly of the apparatus. FIGS. 2A and 2B show a three-dimensional view of the positioning guide assembly which comprises the tubular positioning guide 2 fixedly attached at a right angle to a worm gear 8 and slidably inserted in a stabilizer cylinder overtube 9. A pivoting center of the worm gear 8 is supported by a lateral guide 13. An opposite lateral guide 10 supports a rocker-switch-type lock and release lever 17 in a space 12. The lock and release lever 17 snaps in and out of a horizontal slot located in a bottom portion of the stabilizer cylinder overtube 9. The horizontal slot is bordered by a pair of lateral edges 21 and 22 of the stabilizer cylinder overtube 9. The lock and release lever 17 pivots about a pin 19 that is slidably inserted in a pair of recesses, with one of which shown as 11. The lock and release lever 17 has a snap-fit edge 20 that reversibly fastens said lock and release lever to a positioning guide control assembly. A top portion of the lock and release lever 17 has a substantially rectangular protuberance 18 that slides in and out of the horizontal slot of the stabilizer cylinder overtube 9. Both the lateral guides 10 and 13 adjoin a pair of bottom panels 14 and 15, respectively, which is configured to reversibly adhere to a skin. In between of both the bottom panels 14 and 15, an open space 16 is provided through which devices pass toward a tissue object. The stabilizer cylinder overtube 9 is irreversibly attached to the bottom panel via a supporting block 23. FIG. 2C shows an edge 25 of the lateral guide 13, which passively gets fastened to a part of the positioning guide control assembly. There is provided a worm shaft holder 24 that reversibly secures a proximal end of a worm shaft during rotation of the worm gear 8. FIG. 2D shows individual components of the tubular positioning guide 2 with a tip 27 and a top portion 26 through which devices pass. The worm gear 8 is attached to one lateral side of an outer wall of the tubular positioning guide and a stabilizer cylinder 28 is attached to an opposite side of the outer wall. Both are fixedly attached to the outer wall. The stabilizer cylinder 28 stabilizes the tubular positioning guide during rotation and is slidably encased by a thin non-slip tubular elastomer 29. The tubular elastomer 29 is located in between of an outer wall of the stabilizer cylinder 28 and an inner wall of the stabilizer cylinder overtube 9 and provides friction on both the walls. The positioning guide assembly is non-reusable.

Figure 3:
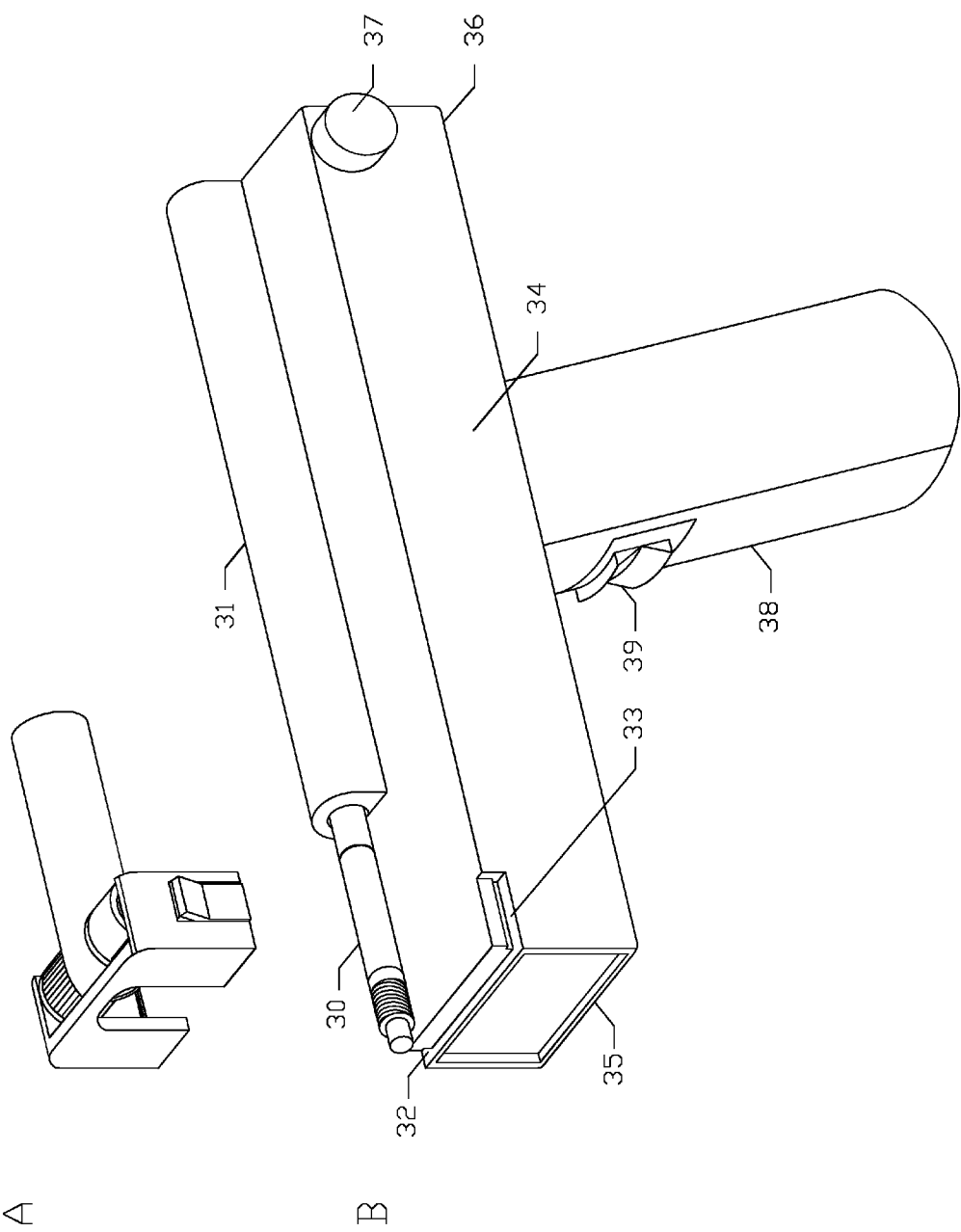
FIG. 3 shows a schematic illustration of an example of a positioning guide control assembly. A proximal end of the positioning guide control assembly shown in FIG. 3B is configured to reversibly couple with a positioning guide assembly shown in FIG. 3A.

FIG. 3 shows a schematic illustration of an example of a positioning guide control assembly. The positioning guide control assembly is provided in one or a plurality of configurations including a longitudinal box configuration with a handle attached to a bottom of said guide control assembly. As shown in FIG. 3B, the positioning guide control assembly comprises a transducer enclosure 34 that anteriorly adjoins a proximal portion 35 and posteriorly a distal portion 36. A handle assembly 38 is attached to a lower wall of the transducer enclosure 34. Both the transducer enclosure 34 and handle assembly 38 house an ultrasound transducer and electric cables, which are connected to a main ultrasonographic machine. Control of the positioning guide control assembly is accomplished by an electric switch 39 located on an anterior part of the handle assembly 39. A pair of notches 32 and 33 are provided for a length on both lateral edges of an upper wall of the proximal portion of the positioning guide control assembly shown in FIG. 3B, which is configured to reversibly couple with a positioning guide assembly shown in FIG. 3A. The proximal portion 35 provides space for solid gel panels and a position alignment assembly and the distal portion 36 houses a power and electronic control assembly. A control knob 37 is located on one lateral wall of the distal portion 36, which is connected to the power and electronic control assembly and provides said power and electronic control assembly with a range of numerical information. An output shaft enclosure 31 is attached longitudinally to a part of an upper surface of the transducer enclosure 34. A worm shaft 30 is reversibly connected to a gear shaft protruding from the output shaft enclosure 31.

Figure 4:
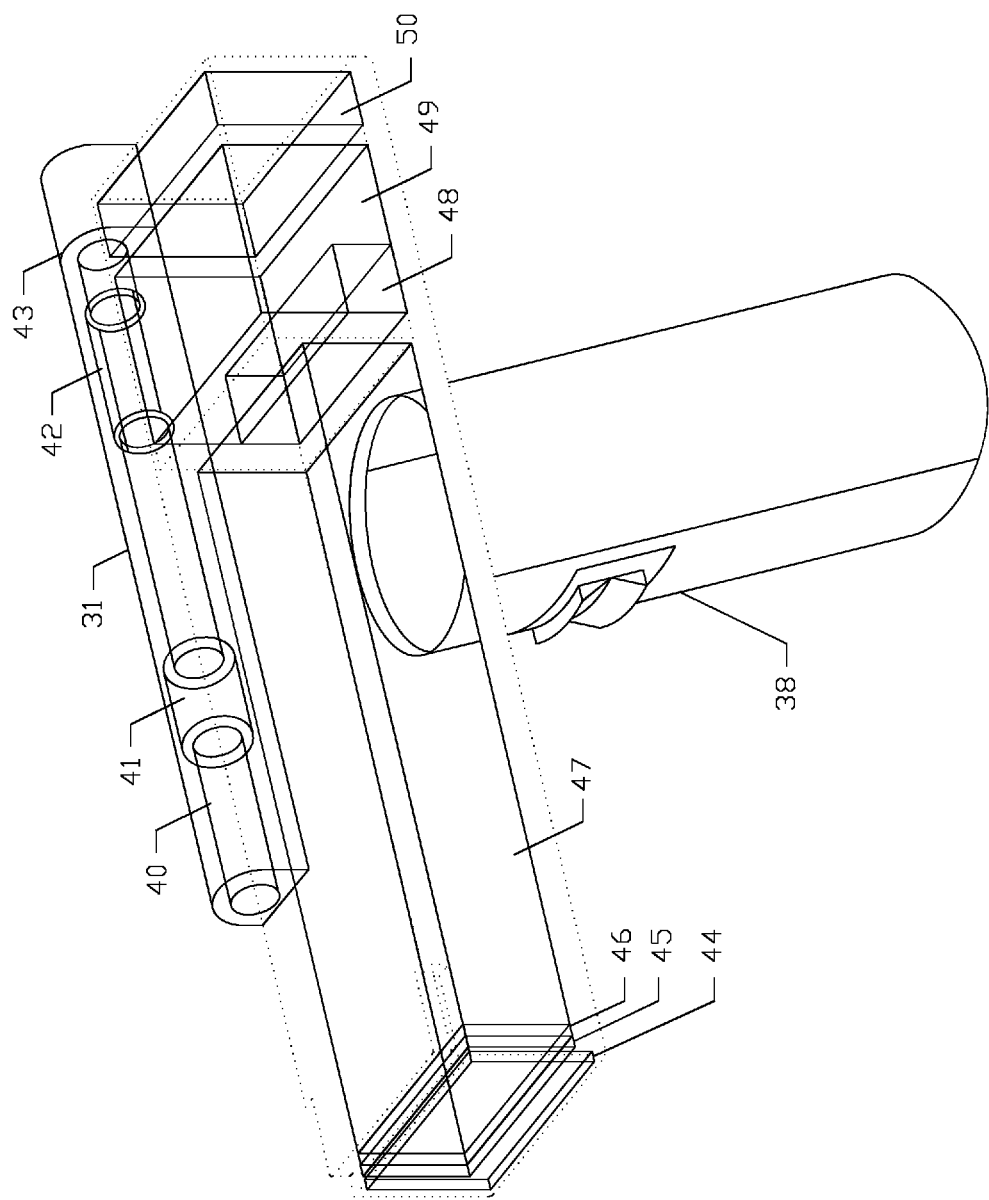
FIG. 4 shows a schematic example of individual compartments of the positioning guide control assembly.

FIG. 4 shows a schematic see-through illustration of an example of individual compartments of the positioning guide control assembly. The proximal portion of the positioning guide control assembly is provided in one or a plurality of configurations, including rectangularly tubular compartments 44 and 46 to reversibly hold a pair of solid gel panels to enhance ultrasound transmission between a face of the transducer and a tissue, and another rectangularly tubular compartment 45 located in between of the spaces 44 and 46 to house a position alignment assembly. Distal to the compartment 46, there is provided a rectangularly tubular space for a compartment 47 for the transducer, a battery compartment 48, a compartment 49 for a gearbox of a positioning control assembly and a compartment 50 for an electronic control assembly. A lower wall of the transducer compartment 47 adjoins an open upper part of the tubular handle assembly 38. The output shaft enclosure 31 is provided in one or a plurality of tubular configurations, which comprises an output shaft housing 40, a housing 41 for a rolling-element bearing portion of the output shaft, a shaft gear housing 42 and a distal portion 43. A bottom of the shaft gear housing 42 is open to an upper part of the gearbox compartment 49 to allow meshing of the shaft gear with a gear of the gearbox.

Figure 5:
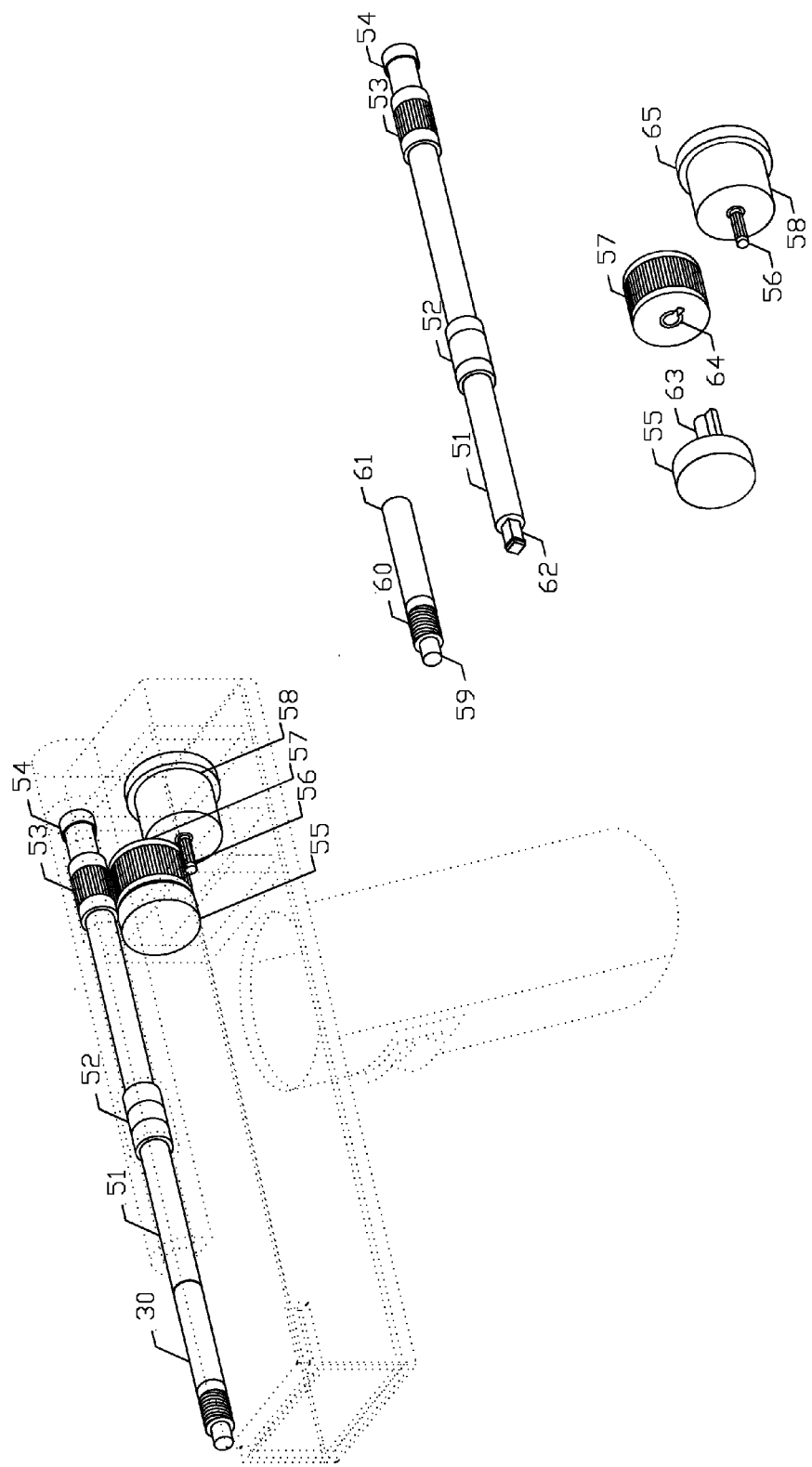
FIG. 5 shows a schematic example of individual components of a positioning control assembly of the positioning guide control assembly.

FIG. 5 shows a schematic example of a positioning control assembly, provided in one or a plurality of configurations including a parallel spur gear arrangement, which comprises an electric motor 58, a pair of spur gears 57 and 53, and an angle encoder 55. The electric motor is irreversibly fastened by a flange 65 to a distal wall of the positioning control assembly, with its rotor 56 protruding longitudinally along the axis. A protruded portion of the rotor 56 is configured as a longitudinal spur gear that meshes in parallel with the cylindrical spur gear 57. The cylindrical spur gear 57 is connected coaxially to the angle encoder 55 by coupling of a central rotatable rod 63 of said angle encoder with a central tubular space 64 of said spur gear. The angle encoder is fastened to a proximal wall of the positioning control assembly. The angle encoder 55 measures rotational displacements of said cylindrical spur gear 57 and is electronically connected to the power and electronic control assembly that relays an electronic information from said angle encoder of rotational displacements of said cylindrical spur gear 57 to the position alignment assembly. The cylindrical spur gear 57 meshes with another longitudinal spur gear 53 that merges with an output shaft 51 located inside the output shaft enclosure. The output shaft 51 is provided in one or a plurality of configurations and transfers axial rotation to the worm shaft 30. Referring to FIG. 4, a proximal end 62 of the output shaft 51 protrudes from an opening located at a proximal end of the output shaft enclosure 31 and is configured to be reversibly connected to a distal end 61 of the worm shaft 30. The worm shaft 30 comprises a proximal end 59, the worm 60 and the distal end 61 that has a longitudinal slot inside for a length to accommodate the proximal end 62 of the output shaft 51. Referring to FIG. 4, the distal portion 43 of the output shaft enclosure 31 provides a central tubular cup 54 to accommodate a distal end of the output shaft for axial rotation. Referring to FIG. 3, the switch 39 of the handle assembly 38 is electrically connected to the positioning control assembly and is configured to turn on for a controllably variable duration and off the electric motor 58. Rotations of the electric motor 58 are transmitted to the output shaft 51 that in turn rotates the worm shaft 30 of the worm drive arrangement for the positioning guide assembly. Transfer of rotational torque of the output shaft 51 to the worm shaft 30 is assisted by a rolling-element bearing arrangement 52 that is configured to reduce friction between the output shaft enclosure and the output shaft.

Figure 6:
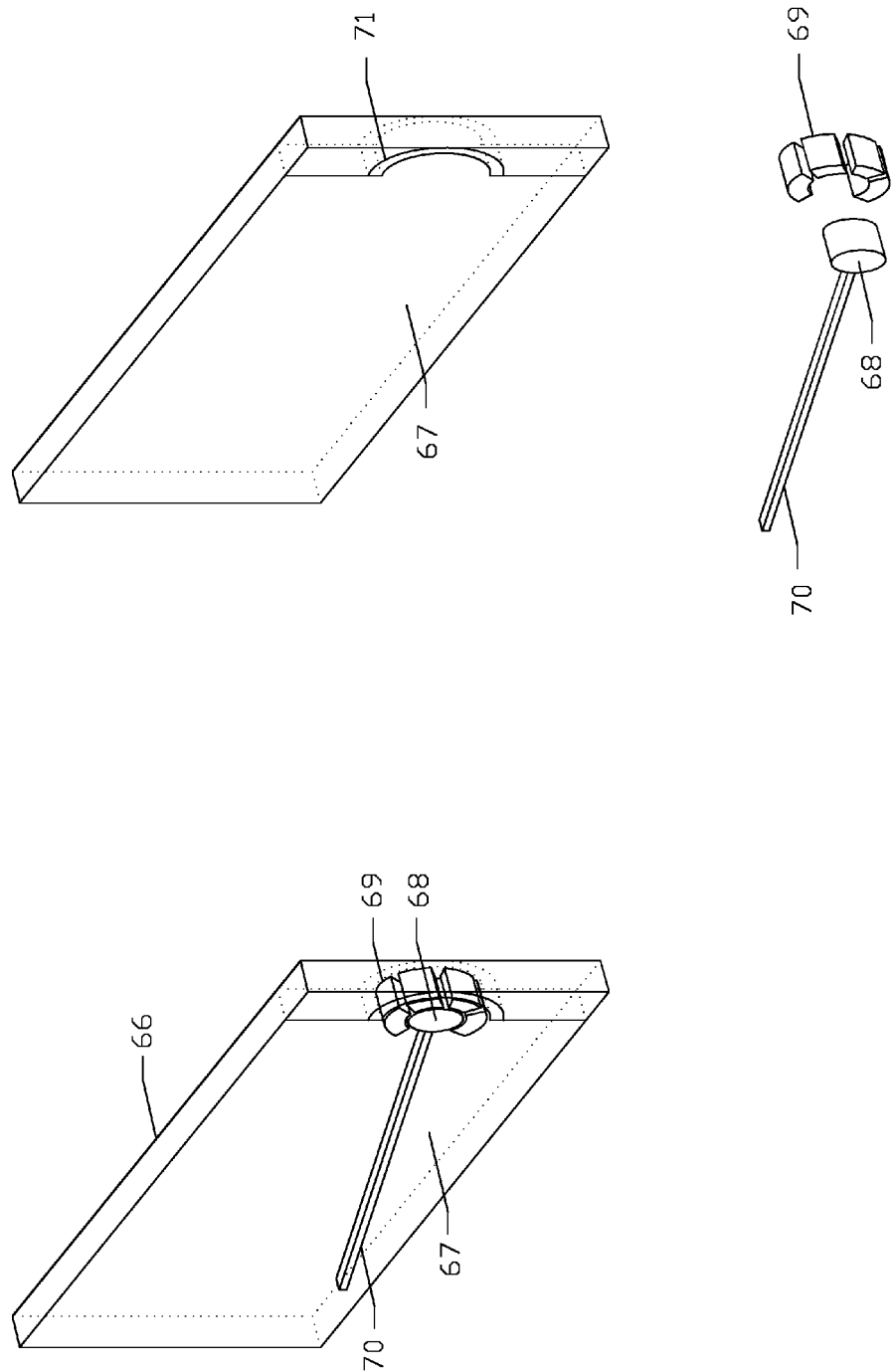
FIG. 6 shows a schematic illustration of an example of a galvanometer-type position alignment assembly.

FIG. 6 shows a schematic illustration of an example of a position alignment assembly, provided in one or a plurality of electromechanical configurations, which comprises a substantially ultrasound-transparent flat rectangular box 66 and an electromagnetic pointing device 68~70. The flat rectangular box 66, provided in one or a plurality of configurations, is located proximal to the face of the transducer, which is made of substantially ultrasound-transparent polymer(s), filled with one or a plurality of type(s) of substantially ultrasound-transparent liquid and leakproof. In one example, the position alignment assembly comprises a galvanometer-type electromagnetic pointing device that uses varying electric current or electric resistance to radially move a linear movable pointer 70 around a center of said device. The linear movable pointer 70 is configured to protrude into a space 67 in the flat rectangular box 66, to move inside said flat rectangular box from side to side and to block ultrasound transmission, which is visualized in an ultrasonographic view. The linear movable pointer 70 is configured to have a means to reduce drag upon moving inside the liquid. The galvanometer-type device comprises a U-shaped set of electromagnetic windings 69 circumferentially surrounding a pivoting wire core 68 and the linear movable pointer 70 connected to the pivoting wire core 68. A semicircular wall 71 immobilizes the windings 69 in a U-shaped configuration. Both the pivoting wire core 68 and the windings 69 are electrically connected to the power and electronic control assembly. All components of the galvanometer-type electromagnetic pointing device are configured as waterproof. Both proximal and distal surfaces of the flat rectangular box contact with a pair of the solid gel panels to enhance ultrasound transmission.

Figure 7:
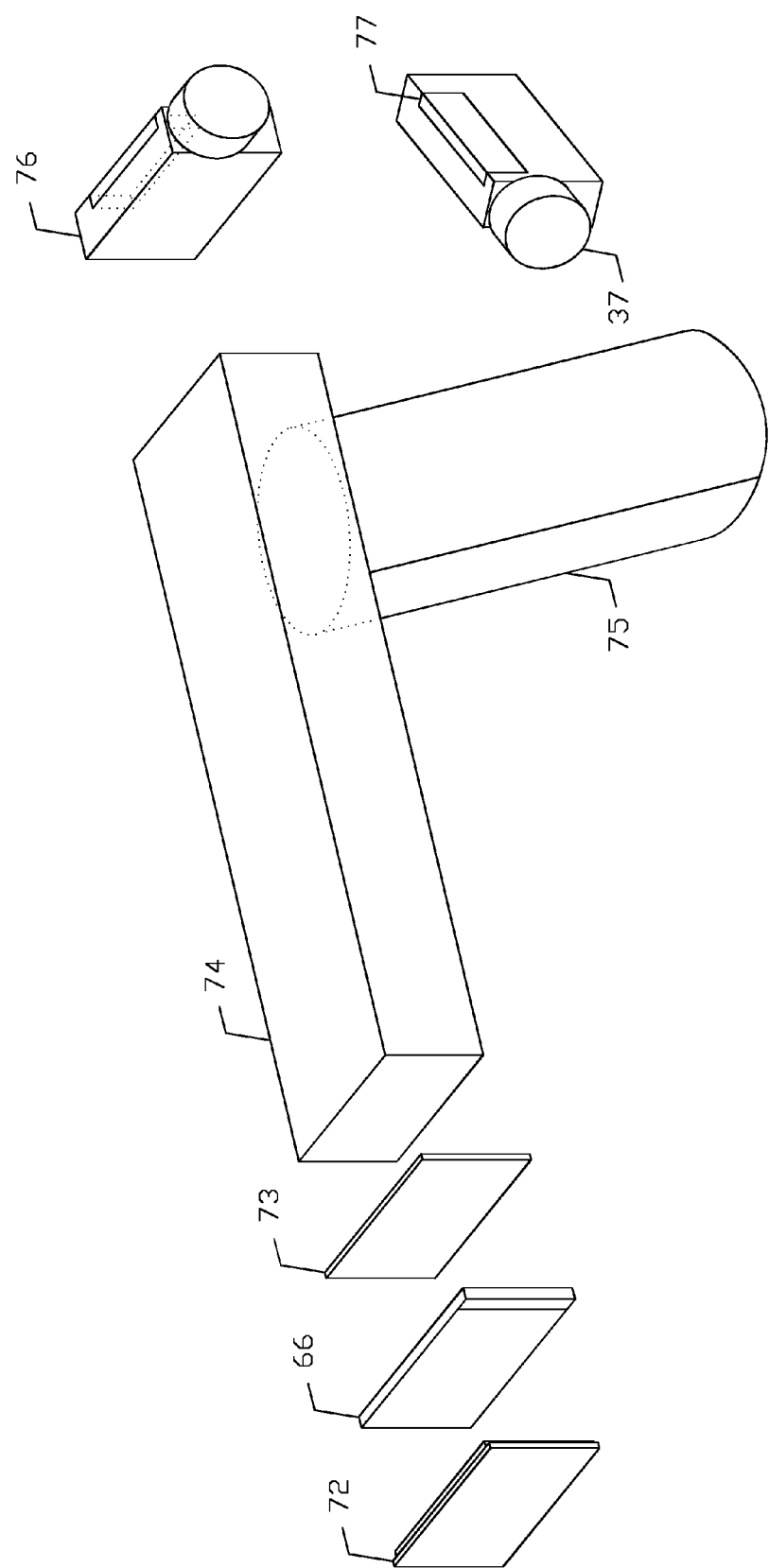
FIG. 7 depicts a schematic illustration of components housed in the positioning guide control assembly.

FIG. 7 depicts a schematic illustration of components housed in the positioning guide control assembly. A non-reusable solid gel panel 72 slidably is placed in front of the position alignment assembly 66 and a second solid gel panel 73 is placed in between of said position alignment assembly 66 and an ultrasound transducer 74. The solid gel panel 72 contacts with a skin overlying a tissue object. The transducer 74 is configured to be electrically connected to a main ultrasonographic machine through electric cables housed in a handle portion 75 attached to a bottom of said transducer. The electronic control assembly 76 having an integrated circuit board with a segment digital display 77 is placed in the distal portion of the positioning guide control assembly. The segment digital display 77 is configured to be seen through the distal wall of said positioning guide control assembly. The rotatable knob 37 is connected to the electronic control assembly 76, which is configured to provide the integrated circuit board with a range of numerical information.

FIG. 8 illustrates an schematic example of mechanisms of locking and unlocking of the tubular positioning guide. FIGS. 8A and 8C show an unlocked configuration of the tubular positioning guide. Once the protuberance 18 of the lock and release lever 17 is inserted in the horizontal slot of the stabilizer cylinder overtube 9, it widens a circumference and an inner tubular space of the stabilizer cylinder overtube 9 and releases the non-slip elastomer 29 from a plurality of horizontally linear threads 78 and 79 located on an inner wall of the stability cylinder overtube 9. Widening of the circumference and the inner tubular space of the stabilizer cylinder overtube allows axial rotation of both the non-slip elastomer 29 and the stabilizer cylinder 28. FIGS. 8B and 8D show a locked configuration of the tubular positioning guide. The protuberance 18 of the lock and release lever 17 pivotably moves out from the horizontal slot of the stabilizer cylinder overtube 9, which allows said stabilizer cylinder overtube to circumferentially shrink and fasten both the non-slip elastomer 29 and the stabilizer cylinder 28 thereby preventing axial rotation of said elastomer and said stabilizer cylinder.

Figure 9:
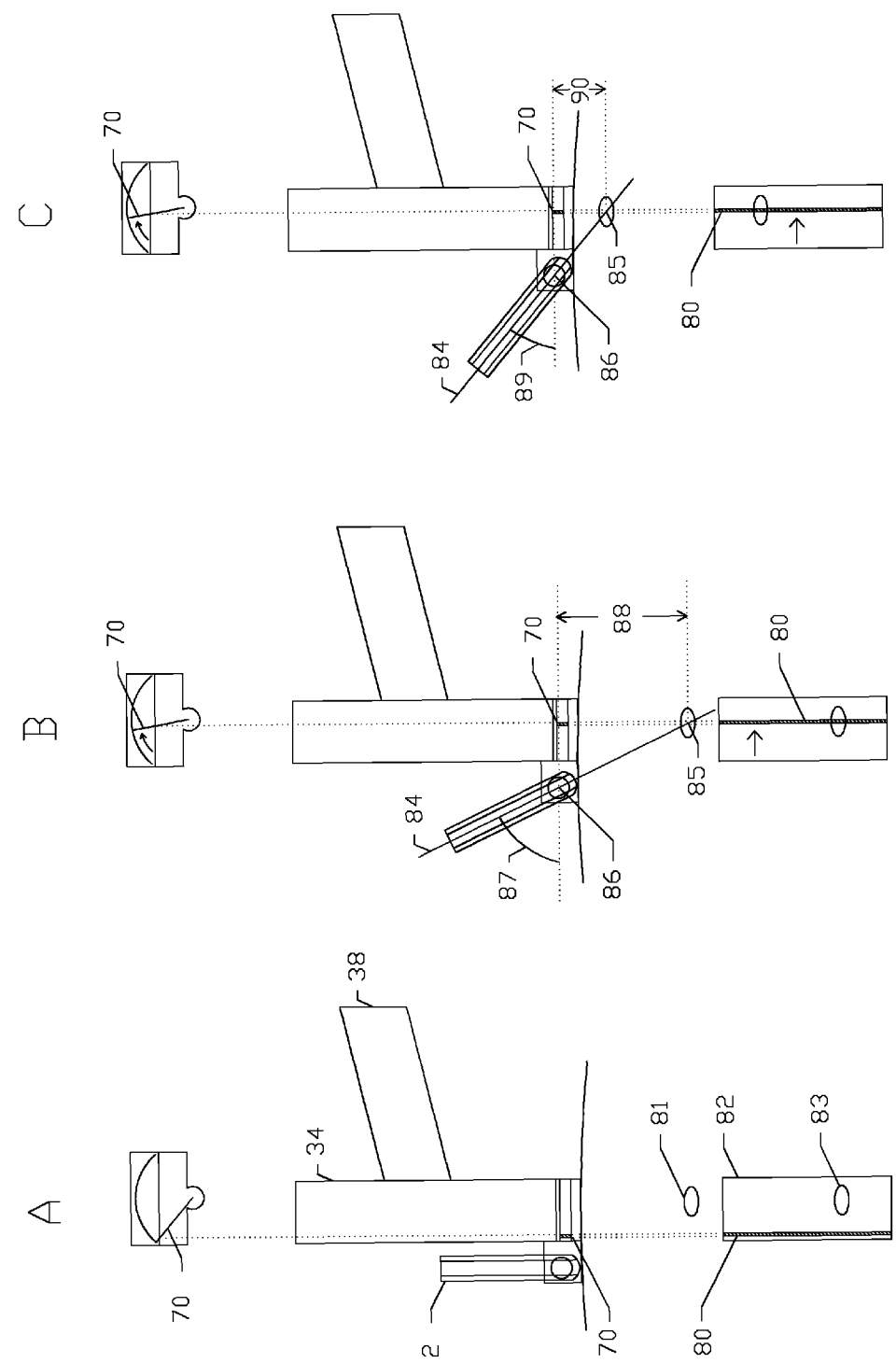
FIG. 9 depicts a schematic illustration of an example of a method of coordination of an angular rotation of the tubular positioning guide with a linear movement of a linear movable pointer of the position alignment assembly to aim at a center of a tissue object.

FIG. 9 depicts a schematic illustration of an example of a method of coordination of an angular rotation of the tubular positioning guide 2 with a horizontal movement of the linear movable pointer 70 of the position alignment assembly to aim at a center 85 of a tissue object 81. The position alignment assembly is configured to coordinate angulation of the tubular positioning guide with horizontal movement of the linear movable pointer in ways to have a longitudinal axis of the tubular positioning guide cross the linear shadow line at the center of the tissue object. In 9A, 9B and 9C, upper drawings represent a schematic top-down view of the position alignment assembly showing the linear movable pointer 70 radially moving. Mid drawings show a schematic profile view of the apparatus placed atop a skin overlying the tissue object 81. Lower drawings depict a schematic ultrasonographic two-dimensional view 82 seen in a monitor of an ultrasonographic machine. As illustrated in FIG. 9A, once the apparatus is placed on the skin above the tissue object 81, the linear movable pointer 70 generates a linear shadow line 80 in the two-dimensional view 82 by blocking off an ultrasonographic transmission. In this example, the linear shadow line 80 is seen away in a distance from an ultrasonographic image 83 of the tissue object 81. In FIG. 9B, based on a vertical distance 88 from the transducer face to the center 85 of tissue object 81, the tubular positioning guide 2 is rotated about a rotation center 86 to an angle 87, enabling the longitudinal axis 84 of said tubular positioning guide to cross the center 85 of the tissue object 81. The rotation of said tubular positioning guide electronically translates into a horizontal movement of the linear movable pointer 70 to a position vertically linear up from the center 85 of the tissue object 81, which is monitored real-time in the two-dimensional ultrasonographic view 82. A crossing of the linear shadow line 80 through the center 85 of the tissue object 81 indicates a crossing of the longitudinal axis 84 of the tubular positioning guide 2 through said center 85 of said tissue object 81. FIG. 9C illustrates an example of a more acute angle 89 of the tubular positioning guide calculated from a shorter vertical distance 90 between the center 85 of the tissue object 81 and the transducer face while the linear shadow line 80 moves the same distance as in FIG. 9B.

FIG. 10 illustrates a schematic example of a sequence of action of the present invention. FIG. 10A shows an uncoupled set of a positioning guide control assembly and a positioning guide assembly. In this illustration, a tubular positioning guide remains fastened by a disengaged lock and release lever to prevent rotation of said tubular positioning guide. Once coupled together as shown in FIG. 10B, the lock and release lever of the positioning guide assembly engages the positioning guide control assembly to fasten said positioning guide assembly to the positioning guide control assembly. The engaged lock and release lever frees the tubular positioning guide for rotation. In FIG. 10C, the positioning guide control assembly rotates the tubular positioning guide to a certain angle for guiding an invasive tubular device to a tissue object. Following confirmation of an accurate angulation of the tubular positioning guide, the positioning guide assembly attaches to a skin overlying the tissue object and separates from the positioning guide control assembly, as shown in FIG. 10D. The lock and release lever reverts back to the disengaged position that fastens the tubular positioning guide.

FIG. 11 illustrates schematic examples of various configurations of the tubular positioning guide of the apparatus of the present invention. For conventional needle biopsy procedures, FIG. 11A shows a configuration for a range of fixed gauges of an inner tubular space to accommodate a range of sizes of invasive devices. FIGS. 11B and 11C show configurations of a tubular body to fasten needles and probes for diagnostic and therapeutic purposes which require a steady maintenance of a position of an invasive device for a duration of the procedure. One example uses a pair of depressible rocker-switch type knobs located longitudinally in a tubular wall, as shown in FIG. 11-B1. An internal lumen of the tubular guide is narrowed by pushing the pair of the depressible knobs, which holds fast an invasive device inside the internal lumen, as shown in FIG. 11B-2. Another example shown in FIG. 11C uses a cap with internal threads which rotatably narrow an internal lumen of a threaded tubular guide and fasten an invasive device inside said tubular guide. FIG. 11D shows a configuration of a semi-circular tube which allows an open access to said tubular guide and insertion of more than one device during one session of a procedure and unobstructed interchangeable removal of devices.

It is to be understood that the aforementioned description of the apparatus and methods is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. A powered stereotactic positioning guide apparatus, comprising:
   a positioning guide means, and a positioning guide control means;
   wherein said positioning guide means comprises a tubular positioning guide, a pivotable means, a lock and release means and a securing means, wherein said positioning guide means is configured to synchronize coupling said positioning guide means with the positioning guide control means for operational control of said positioning guide means by said positioning guide control means with letting the pivotable means be rotatable, wherein said positioning guide means is configured to synchronize uncoupling said positioning guide means from said positioning guide control means with locking said pivotable means so as to guide an invasive tubular device inside said positioning guide means slidably passing therethrough in a range of insertion angle to a tissue object, wherein said positioning guide means is configured to be independently operable following uncoupling from said positioning guide control means, and wherein said positioning guide means is configured to rotationally adjust and reversibly lock said tubular positioning guide for the insertion angle of the invasive tubular device; and
   wherein said positioning guide control means comprises an electromagnetic pointing device, a positioning control means, a power and electronic control means, an ultrasound transducer enclosure and a handle, wherein said positioning guide control means is configured to visually locate the tissue object by the electromagnetic pointing device of said positioning guide control means in a visualized ultrasonographic field, wherein said positioning guide control means is configured to be electrically powered to align a longitudinal axis of said positioning guide means with the tissue object in the visualized ultrasonographic field, and wherein said positioning guide control means is configured to electronically synchronize locating the tissue object by said electromagnetic pointing device with aligning the longitudinal axis of said positioning guide means with the tissue object.

2. The powered stereotactic positioning guide apparatus according to claim 1,
   wherein said tubular positioning guide comprises a tubular conduit, wherein said tubular conduit is configured to slidably pass the invasive tubular device therethrough to reach the tissue object, wherein said tubular positioning guide is configured to fixedly join the pivotable means at a right angle in a cross configuration, and wherein said tubular positioning guide is configured to rotate about a joint with the pivotable means;
   wherein said pivotable means comprises a worm gear which meshes with a worm of the positioning guide control means, wherein said pivotable means is configured to transmit powered rotational torque from said worm of said positioning guide control means to the tubular positioning guide by a worm gear arrangement made of said worm of said positioning guide control means and said worm gear of said pivotable means, wherein said pivotable means is configured to pivot the tubular positioning guide about the joint with said tubular positioning guide, wherein said pivotable means comprises a stabilizer cylinder located opposite to and coaxially with said worm gear of said pivotable means, and wherein said stabilizer cylinder of said pivotable means is configured to stabilize said tubular positioning guide during rotation of said tubular positioning guide about said pivotable means;
   wherein said lock and release means comprises a lock and release lever and a receiving slot disposed on a stabilizer cylinder overtube of the securing means, wherein said lock and release lever is configured to be reversibly and fastenably inserted in said receiving slot, wherein the stabilizer cylinder overtube is configured to squeezably encase the stabilizer cylinder of the pivotable means, wherein said lock and release means comprises a snap-fit edge on one end of said lock and release lever, wherein said snap-fit edge of said lock and release lever is configured to snap in a corresponding notch of the positioning guide control means so as to reversibly fasten said positioning guide means to said positioning guide control means, wherein said lock and release lever is configured to be pivotably inserted to said receiving slot of said stabilizer cylinder overtube to release said stabilizer cylinder of said pivotable means from said stabilizer cylinder overtube so as to let said pivotable means be rotatable and synchronizably couple the positioning guide means with the positioning guide control means, and wherein said lock and release lever is configured to pivotably move out from said receiving slot of said stabilizer cylinder overtube to lock said stabilizer cylinder of said pivotable means by said stabilizer cylinder overtube so as to lock said pivotable means by said stabilizer cylinder overtube and synchronizably uncouple said positioning guide means from said position guide control means; and
   wherein said securing means comprises a flat wall configured to face the skin of the tissue object, a vertical sidewall adjoining each side of said flat wall and the stabilizer cylinder overtube fixedly attached to an inner surface of said flat wall, wherein an inner surface of a first vertical sidewall of said securing means is configured to rotatably hold the worm gear of the pivotable means, and wherein an inner surface of a second vertical sidewall of said securing means is configured to provide the lock and release lever with a pivotable slot.

3. The powered stereotactic positioning guide apparatus according to claim 2,
   wherein said worm gear is configured to transmit the rotational torque from a gear output device of the positioning guide control means to the tubular positioning guide, wherein said worm gear is configured to be fixedly attached at a right angle to said tubular positioning guide thereof at a distal end of said tubular positioning guide, and wherein said worm gear is configured to reversibly form the worm gear arrangement with the worm positioned on a worm shaft of said gear output device of said positioning guide control means;

wherein said stabilizer cylinder is configured to stabilize said tubular positioning guide during the rotation of said tubular positioning guide, and wherein said stabilizer cylinder is configured to be fixedly attached at a right angle to said tubular positioning guide opposite to and coaxially with said worm gear of said pivotable means; and wherein the pivotable means further comprises a tubular elastomer, wherein said tubular elastomer is configured be located inside the stabilizer cylinder overtube of the securing means of the positioning guide means, wherein said tubular elastomer is configured to slidably encase said stabilizer cylinder, wherein said tubular elastomer is configured to be concentrically squeezable by said stabilizer cylinder overtube of said securing means, and wherein said tubular elastomer is configured to provide said stabilizer cylinder with reversible friction to reversibly fasten said stabilizer cylinder by said stabilizer cylinder overtube.

4. The powered stereotactic positioning guide apparatus according to claim 1, wherein the positioning guide control means further comprises:

an ultrasound transducer;

wherein said electromagnetic pointing device is configured to be located in front of and in parallel with a face of the ultrasound transducer, wherein said electromagnetic pointing device is configured to be powered and controlled by the power and electronic control means, wherein said electromagnetic pointing device is configured to be electronically synchronized with the positioning control means by said power and electronic control means, wherein said electromagnetic pointing device comprises a linear movable pointer having one end of said linear movable pointer connected to a pivotable center surrounded by a plurality of electromagnetic windings, wherein said linear movable pointer of said electromagnetic pointing device is configured to produce a linear shadow line in the visualized ultrasonographic field by blocking transmission of a portion of both non-divergent and divergent ultrasonographic waves from said ultrasound transducer passing through said electromagnetic pointing device to the tissue object, and wherein said electromagnetic pointing device is configured to synchronize radial movement of said linear movable pointer with rotatably aligning the longitudinal axis of the tubular positioning guide of the positioning guide means with the tissue object by said positioning control means;

wherein said positioning control means comprises a gearbox parallel spur gear arrangement having a gear output device and an angle encoder coaxially attached to said parallel spur gear arrangement to measure rotational displacement of said parallel spur gear arrangement, wherein said rotational displacement of said parallel spur gear arrangement is configured to be electronically synchronized with said electromagnetic pointing device by the power and electronic control means, wherein said positioning control means comprises a worm located at a proximal end of a worm shaft of said gear output device, wherein said worm is configured to mesh with a worm gear of the pivotable means of the positioning guide means, and wherein said positioning control means is configured to pivotably and controllably rotate the tubular positioning guide of the positioning guide means by the worm gear arrangement made of said worm of said positioning control means and said worm gear of said pivotable means of said positioning guide means;

wherein said power and electronic control means is provided in an electronic configuration, wherein said power and electronic control means is configured to electronically synchronize locating the tissue object by said electromagnetic pointing device with aligning the longitudinal axis of said tubular positioning guide of said positioning guide means with the tissue object;

wherein said ultrasound transducer enclosure is configured to house the electromagnetic pointing device, the ultrasound transducer, the positioning control means, and the power and electronic control means from a proximal end to a distal end of said transducer enclosure in tandem, wherein the electromagnetic pointing device is placed in front of and in parallel with a face of the ultrasound transducer, and wherein said transducer enclosure is configured to align with the ultrasound transducer along longitudinal and horizontal axes of said ultrasound transducer; and wherein said handle is provided in a tubular configuration, wherein said handle is configured to be connected to a lower wall of the ultrasound transducer enclosure, and wherein said handle comprises an electric switch synchronizably controlling the electromagnetic pointing device and the positioning control means.

5. The powered stereotactic positioning guide apparatus according to claim 4, wherein the electromagnetic pointing device is configured to transmit the non-divergent and divergent ultrasonographic waves from the ultrasound transducer through said electromagnetic pointing device to the tissue object except that the linear movable pointer of said electromagnetic pointing device is configured to block transmission of said non-divergent and divergent ultrasonographic waves.

6. The powered stereotactic positioning guide apparatus according to claim 4, wherein the electromagnetic pointing device is configured to be waterproof.

7. The powered stereotactic positioning guide apparats according to claim 4, wherein said electromagnetic pointing device is configured to be a galvanometer-type device which uses electricity provided by the power and electronic control means to radially move the linear movable pointer about a pivotable center of said linear movable pointer, wherein said linear movable pointer is configured to move in parallel with the face of the ultrasound transducer, wherein said linear movable pointer is configured to block transmission of both the non-divergent and divergent ultrasonographic waves from said ultrasound transducer across said linear movable pointer to the tissue object so as to produce the linear shadow line in the visualized ultrasonographic field, and wherein said linear shadow line is configured to be surrounded by visible non-divergent and divergent ultrasonographic waves in the visualized ultrasonographic field.

8. The powered stereotactic positioning guide apparatus according to claim 4, further comprising:

an electric motor;

wherein the power and electronic control means is configured to drive the electric motor so as to generate and transmit the rotational torque from the parallel spur gear arrangement to the worm gear of the pivotable means of the positioning guide means, wherein the angle encoder of said parallel spur gear arrangement is configured to electronically measure the rotational displacement of said parallel spur gear arrangement, wherein said angle encoder is configured to provide said power and electronic control means with an electronic information of said rotational displacement of said parallel spur gear arrangement, wherein said power and electronic control means is configured to provide the electromagnetic pointing device with an electricity based on said electronic information of said rotational displacement of said parallel spur gear arrangement so as to controllably and radially move the linear movable pointer of said electromagnetic pointing device, and wherein said power and electronic control means is configured to synchronize generation and transmission of the rotational torque from said parallel spur gear arrangement with radial movement of said linear movable pointer of said electromagnetic pointing device.

9. A method of rotating the tubular positioning guide of the positioning guide means of the powered stereotactic positioning guide apparatus according to claim 4, comprising:

providing the powered stereotactic positioning guide apparatus comprising the positioning guide means and the positioning guide control means;

fastenably snapping a snap-fit edge of a lock and release lever of the positioning guide means in a corresponding notch of the positioning guide control means so as to couple said positioning guide means with said positioning guide control means and simultaneously insert the lock and release lever of said positioning guide means into a receiving slot of a stabilizer cylinder overtube of said positioning guide means, wherein insertion of said lock and release lever of said positioning guide means into said receiving slot of said stabilizer cylinder overtube of said positioning guide means is synchronized to release a tubular positioning guide of said positioning guide means from said stabilizer cylinder overtube so as to let said tubular positioning guide of said positioning guide means be rotatable;

powering up the positioning guide control means;

placing a proximal end of the powered stereotactic positioning guide apparatus on a skin overlying a tissue object, wherein a flat wall of a securing means of the positioning guide means contacts the skin;

visualizing the area of the tissue object and the tissue object in a visualized ultrasonographic field of a main ultrasonographic machine;

pushing the electric switch of the handle to drive an electric motor of the positioning guide control means so as to generate and transmit a rotational torque from said parallel spur gear arrangement to said worm gear of the pivotable means of the positioning guide means;

electronically measuring the rotational displacement of said parallel spur gear arrangement by said angle encoder coaxially attached to said parallel spur gear arrangement;

providing a power and electronic control means with an electronic information of said rotational displacement of said parallel spur gear arrangement;

providing the electromagnetic pointing device with an electricity from the power and electronic control means based on said electronic information of said rotational displacement of said parallel spur gear arrangement so as to controllably and radially move the linear movable pointer of said electromagnetic pointing device;

synchronizing generation and transmission of the rotational torque from said parallel spur gear arrangement with radial movement of said linear movable pointer of said electromagnetic pointing device by the power and electronic control means; and continuing to rotate the worm gear of the pivotable means fixedly attached to the tubular positioning guide so as to rotate the tubular positioning guide of the positioning guide means until the linear shadow line produced by the linear movable pointer of the electromagnetic pointing device intersects the tissue object in the visualized ultrasonographic field.

10. A method of producing a linear shadow line in a visualized ultrasonographic field, comprising:

providing a powered stereotactic positioning guide apparatus according to claim 4;

fastenably snapping a snap-fit edge of a lock and release lever of the positioning guide means in a corresponding notch of the positioning guide control means so as to couple said positioning guide means with said positioning guide control means and simultaneously insert the lock and release lever of said positioning guide means into a receiving slot of a stabilizer cylinder overtube of said positioning guide means, wherein insertion of said lock and release lever of said positioning guide means into said receiving slot of said stabilizer cylinder overtube of said positioning guide means is synchronized to release a tubular positioning guide of said positioning guide means from said stabilizer cylinder overtube so as to let said tubular positioning guide of said positioning guide means be rotatable;

powering up the positioning guide control means;

placing a proximal end of the powered stereotactic positioning guide apparatus on a skin overlying a tissue object, wherein a flat wall of a securing means of the positioning guide means contacts the skin;

visualizing the area of the tissue object and the tissue object in the visualized ultrasonographic field of a main ultrasonographic machine;

transmitting unselected non-divergent and divergent ultrasonographic waves from an ultrasound transducer across said electromagnetic pointing device to the tissue object; and blocking transmission of a portion of the unselected non-divergent and divergent ultrasonographic waves from the ultrasound transducer passing through said electromagnetic pointing device by the linear movable pointer of said electromagnetic pointing device, wherein a blocked portion of the unselected non-divergent and divergent ultrasonographic waves produces no visible ultrasonographic signal in the visualized ultrasonographic field, and wherein said blocked portion of the unselected non-divergent and divergent ultrasonographic waves is surrounded by transmitted and visible unselected non-divergent and divergent ultrasonographic waves in the visible ultrasonographic field.

11. A method of guiding an invasive tubular device to reach a tissue object, comprising:

providing a powered stereotactic positioning guide apparatus comprising a positioning guide means and a positioning guide control means;

fastenably snapping a snap-fit edge of a lock and release lever of the positioning guide means in a corresponding notch of the positioning guide control means so as to couple said positioning guide means with said positioning guide control means and simultaneously insert the lock and release lever of said positioning guide means into a receiving slot of a stabilizer cylinder overtube of said positioning guide means, wherein insertion of said lock and release lever of said positioning guide means into said receiving slot of said stabilizer cylinder overtube of said positioning guide means is synchronized to release a tubular positioning guide of said positioning guide means from said stabilizer cylinder overtube so as to let said tubular positioning guide of said positioning guide means be rotatable;

powering up the positioning guide control means;

placing a proximal end of the powered stereotactic positioning guide apparatus on a skin overlying a tissue object, wherein a flat wall of a securing means of the positioning guide means contacts the skin;

visualizing an area of the tissue object and the tissue object in a visualized ultrasonographic field of a main ultrasonographic machine;

pushing an electric switch of a handle to radially move a linear movable pointer of an electromagnetic pointing device and synchronizably drive an electric motor of the positioning guide control means so as to pivotably rotate the tubular positioning guide, wherein said linear movable pointer produces a linear shadow line in the visualized ultrasonographic field, and wherein radial movement of said linear movable pointer is synchronized with pivotable rotation of said tubular positioning guide of the positioning guide means;

aligning the linear shadow line with the tissue object in the visualized ultrasonographic field in a way said linear shadow line intersects said tissue object;

pivotably withdrawing the lock and release lever of the positioning guide means from the receiving slot of the stabilizer cylinder overtube to lock a stabilizer cylinder of a pivotable means by said stabilizer cylinder overtube so as to lock said pivotable means by said stabilizer cylinder overtube, wherein withdrawal of said lock and release lever of said positioning guide means from said receiving slot of said stabilizer cylinder overtube is synchronized to uncouple said positioning guide means from the position guide control means; and detaching the positioning guide control means from the positioning guide means, wherein the flat wall of the securing means of said positioning guide means is securely adhered to the skin overlying the tissue object, wherein the tubular positioning guide of said positioning guide means is immovably aligned with the tissue object in a way a longitudinal axis of said tubular positioning guide intersects said tissue object at an angle so as to direct an invasive tubular device to the tissue object through said tubular positioning guide, and wherein said flat wall of said securing means of said positioning guide means is configured to allow the invasive tubular device to pass therethrough to the tissue object.

* * * * *